(12) United States Patent
Johnson et al.

(10) Patent No.: US 7,833,524 B2
(45) Date of Patent: Nov. 16, 2010

(54) METHOD OF PREPARING BOTULINUM NEUROTOXIN TYPE E LIGHT CHAIN

(75) Inventors: Eric A. Johnson, Madison, WI (US); Marite Bradshaw, Madison, WI (US); Michael Baldwin, Milwaukee, WI (US); Joseph T. Barbieri, New Berlin, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/273,157

(22) Filed: Nov. 18, 2008

(65) Prior Publication Data

US 2009/0182123 A1    Jul. 16, 2009

Related U.S. Application Data

(62) Division of application No. 11/404,289, filed on Apr. 14, 2006, now Pat. No. 7,465,457.

(60) Provisional application No. 60/671,276, filed on Apr. 14, 2005.

(51) Int. Cl.
*C12P 1/04*    (2006.01)
(52) U.S. Cl. .................................. 424/94.67; 435/71.3
(58) Field of Classification Search ....................... None
See application file for complete search history.

(56) References Cited

PUBLICATIONS

Wang et al. (Appl. Environ. Microbiol., 66:4992-4997).*
Fujii et al. (Microbiol. Immunol., 36:213-220, 1992).*
Agarwal et al. (Biochem., 43:6637-6644, 2004).*
Baldwin et al., Prot. Exp. Purif., 37:187-195, 2004.*
CRC Handbook of Chemistry and Physics, 78th edition, CRC Press, 1997, p. 2-53.
Cai S & Singh B, Biochemistry 40:4693-4702 (2001).
Dineen S, et al., Curr. Microbiol. 46:345-352 (2003).
Kadkhodayan S, et al., Protein Expr. Purif. 19: 125-130 (2000).
Kurazono H, et al., J. Biol. Chem. 267: 1472 1-14729 (1992).
LaPenotiere H, et al., Toxicon 33: 1383-1386 (1999).
Li L & Singh B, Protein Expr. Purif. 17:339-344 (1999).
Rossetto 0, et al., Toxicon 39: 1 15 1-1 159 (2001).
Zhou L, et al.,Biochemistry 34: 15 175- 15 18 1 (1995).
Li Y, et al., Biochemistry 33:7014-7020 (1994).

\* cited by examiner

*Primary Examiner*—Robert B Mondesi
*Assistant Examiner*—Brian J Gangle
(74) *Attorney, Agent, or Firm*—Quarles & Brady, LLP

(57) ABSTRACT

The present invention provides a preparation of botulinum toxin light chain type A or E, wherein the preparation is both catalytically active and soluble. Preferably, the preparation consists essentially of amino acid residues 1 through 425 of the botulinum toxin light chain type A. A method of screening inhibitors is also provided, wherein the method comprises exposing a test inhibitor to the preparation of botulinum toxin light chain type A and evaluating the biological activity of the preparation. In another embodiment, a method of providing a catalytically active, soluble preparation of botulinum toxin light chain, type A is provided, wherein the method comprises obtaining an expression vector comprising a DNA sequence encoding amino acid residues 1-425 and expressing a polypeptide.

3 Claims, 10 Drawing Sheets

LC 1-398

LC 1-448

|         | Loop        | β-sheet   | Loop    | SEQ ID NOS. |
|---------|-------------|-----------|---------|-------------|
| BoNT/A  | TKLKNFTGLFE | FYKLLCVR  | GIITSK  | 15 |
| BoNT/B  | EEISK-EHLAV | YKIQMCKS  | VKAPG   | 16 |
| BoNT/G  | EEISL-EHLVI | YRIAMCKP  | VMYKNTG | 17 |
| BoNT/C  | KVNPE--NMLY | LFTKFCHK  | AIDGRSL | 18 |
| BoNT/D  | KLSSE--SVVD | LFTKVCLR  | LTK     | 19 |
| BoNT/E  | TPITG-RGLVK | KIIRFCKN  | IVSVK   | 20 |
| BoNT/F  | DSIPD-KGLVE | KIVKFCKS  | VIPRKG  | 21 |
| TeNT    | FRNVDGSGLVS | KLIGLCKK  | IIPPTN  | 22 |

Fig. 5

METHOD OF PREPARING BOTULINUM NEUROTOXIN TYPE E LIGHT CHAIN

CROSS-REFERENCE TO RELATED APPLICATION

This application is a divisional of U.S. patent application Ser. No. 11/404,289 filed Apr. 14, 2006, now U.S. Pat. No. 7,465,457 which claims priority to Provisional Patent Application No. 60/671,276 filed Apr. 14, 2005, the entirety of which is hereby incorporated by reference herein.

STATEMENT REGARDING FEDERALLY SPONSORED RESEARCH OR DEVELOPMENT

This invention was made with United States government support awarded by the following agency: NIH AI057153. The United States government has certain rights in this invention.

BACKGROUND OF THE INVENTION

Botulinum neurotoxins (BoNTs) are a group of homologous protein toxins, produced by various strains of *Clostridium botulinum* and in some cases *C. butyricum* and *C. baratii* (Schiavo et al., *Physiol. Rev.* 80:717-766, 2000). BoNTs elicit the characteristic flaccid paralysis of botulism by blocking acetylcholine release at the neuromuscular junction, through the cleavage of proteins involved in exocytosis. The seven serotypes of BoNTs (A-G) are synthesized and released by the clostridia as inactive ~150 kDa protein precursors (Sakaguchi *Pharmacol. Ther.* 19:165-194, 1983; Minton, *Curr. Top. Microbiol. Immunol.* 195:161-194, 1995; Oguma et al., *Microbiol. Immunol.* 39:161-168, 1995; Lacy et al., *J. Mol. Biol.* 291:1091-1104, 1999; Popoff et al., Structural and genomic features of clostridial neurotoxins, in: J. E. Alouf, J. H. Freer (Eds.) Comprehensive Sourcebook of Bacterial Protein Toxins, Academic, London, 1999). The BoNTs are activated by proteolytic cleavage to generate disulfide-linked di-chain toxins (Sakaguchi, supra, 1983; Minton, supra, 1995; Oguma et al., supra, 1995; Lacy et al., supra, 1999; Popoff et al., supra, 1999), which are amongst the most potent biological poisons known with a mouse lethal dose ($LD_{50}$) of 0.1-1 pg BoNT/g.

The molecular architecture of the BoNTs is conserved and related to their mode of neural intoxication. Heavy chain (HC, ~100 kDa) consists of a C-terminal 50 kDa domain ($HC_C$) involved in specific binding to the pre-synaptic membrane via gangliosides and a protein co-receptor (Dong et al., *J. Cell Biol.* 162:1293-1303, 2003). The N-terminal 50 kDa domain of HC ($HC_N$) is involved in the subsequent translocation of the Light chain (LC, 50 kDa) into the cytosol (Schiavo et al., supra, 2000; Sakaguchi, supra, 1983; Minton, supra, 1995; Oguma et al., supra, 1995; B. D. Lacy et al., supra, 1999; Popoff et al., supra, 1999).

BoNT LCs are zinc metalloproteases that cleave one of three proteins, collectively termed SNARE proteins, which are core components of the machinery that mediates small synaptic vesicle (SSV) fusion, which is responsible for the release of neurotransmitters from nerve terminals. BoNT/A and BoNT/E cleave SNAP-25, $BoNT/C_1$ cleaves syntaxin and SNAP-25, while BoNT/B, /D, /F and /G cleave the vesicle associated membrane protein (VAMP)/synaptobrevin, an integral membrane protein of SSV (Schiavo et al., supra, 2000).

Thus, the BoNTs display exquisite substrate specificity and recognize structurally distinct substrates. This unique substrate specificity may be a model to study substrate recognition by bacterial toxins. However, studies utilizing the holotoxin are constrained by a number of issues, including the intrinsic toxicity of the holotoxin, the lack of tools for genetic manipulation of the clostridia, and the need to activate the holotoxin, a source of inherent error in the analysis of catalytic activity. Studies of other bacterial toxins, such as diphtheria toxin, have overcome these difficulties through the generation of non-toxic catalytic derivatives (Collier, *Toxicon.* 39:1793-1803, 2001). Similarly, the generation of recombinant, catalytically active LC will allow more detailed structure-function studies of BoNTs.

LC has been expressed as a recombinant protein in *E. coli*, with varied success. Early attempts to expressed LC in *E. coli* often resulted in limited expression and poor solubility at concentrations >1 mg/ml (Li et al., *Biochemistry* 33:7014-7020, 1994; LaPenotiere et al., *Toxicon.* 33:1383-1386, 1995; Zhou et al., *Biochemistry* 34:15175-15181, 1995; Kadkhodayan et al., *Protein Express. Purif.* 19:125-130, 2000). The limited solubility of LC purified from the BoNT, suggests that solubility is an intrinsic property of the LC. Recently, Li and Singh (Li et al., *Protein Express. Purif.* 17:339-344, 1999) reported the good expression and purification of recombinant LC, which has been used for kinetic and spectroscopic characterization of toxin action.

BRIEF SUMMARY OF THE INVENTION

In one embodiment, the present invention is a preparation of botulinum toxin light chain type A or E, wherein the preparation is both catalytically active and soluble. Preferably, the preparation consists essentially of amino acid residues 1 through 425 of the botulinum toxin light chain type A or residues 1 through 408 of the botulinum toxin light chain E.

In another embodiment, the invention is a method of screening inhibitors comprising exposing a test inhibitor to the preparation of the present invention and evaluating the biological activity of the preparation. In a preferred version the inhibitors target holotoxin translocation and light chain metalloprotease activity of the botulinum toxin. A method of determining the solubility of the preparation is also provided.

In another embodiment, the invention is a method of providing a catalytically active, soluble preparation of botulinum toxin light chain, type A or E, comprising the steps of: (a) obtaining an expression vector comprising a DNA sequence encoding amino acid residues 1-425 of botulinum toxin light chain A or residues 1-408 of botulinum toxin light chain E, and (b) expressing a polypeptide.

In another embodiment, the invention is an antibody preparation, wherein the antibody has been raised against LC/A 1-425 or LC/E 1-408.

Other embodiments of the present invention will be apparent to one of skill in the art after review of the specification and drawings.

BRIEF DESCRIPTION OF THE SEVERAL VIEWS OF THE DRAWINGS

FIG. 5—Alignment of the C-terminal region of the clostridial Neurotoxins. The C-termini were aligned using the ClustalW algorithm and the structures modeled against BoNTA (3bta) using Swiss-PdbViewer. BoNTs are grouped by amino acid similarity. The cysteine involved in disulfide formation is located within the β-sheet. The residues bolded in the left loop are predicted to form intramolecular hydrogen bonds.

DETAILED DESCRIPTION OF THE INVENTION

Figure 1A:
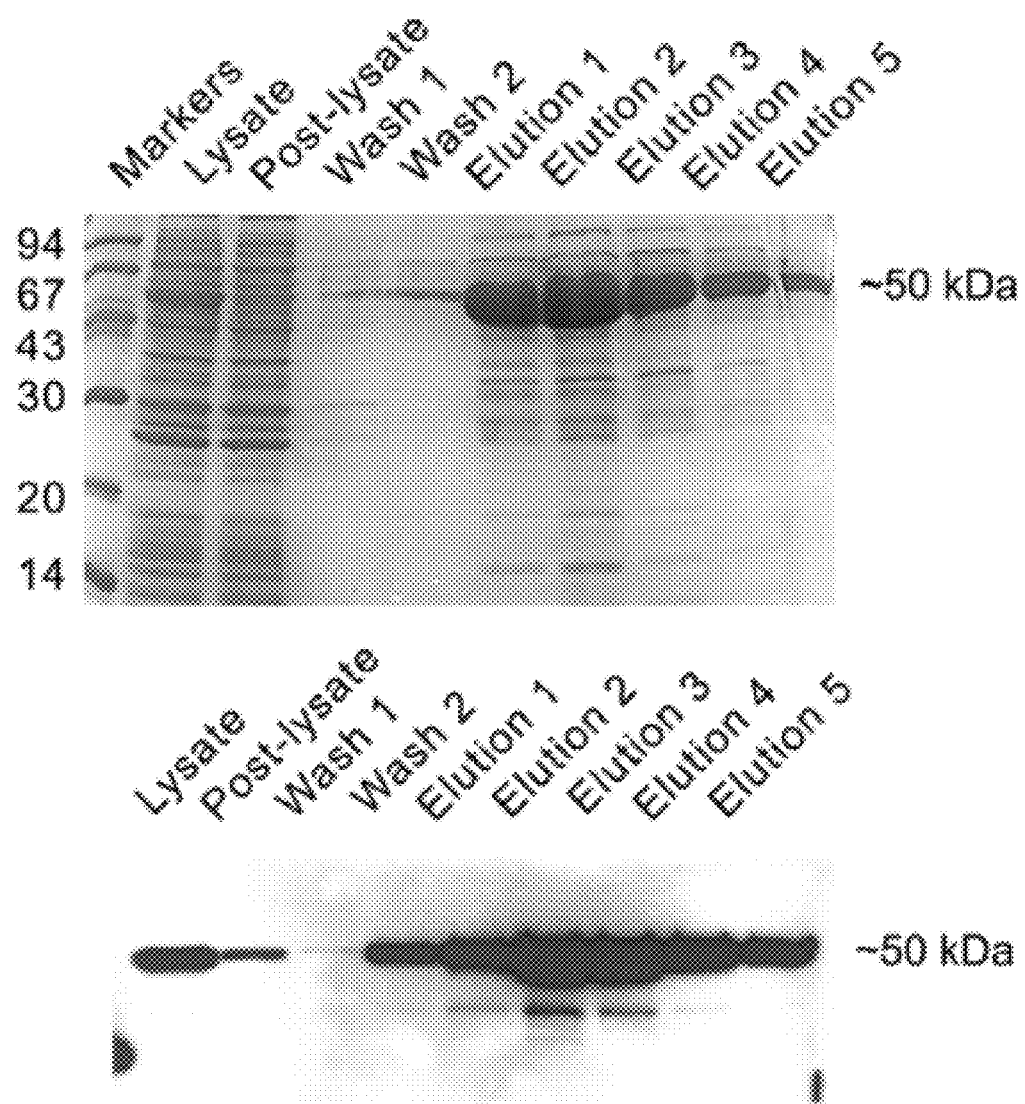
FIG. 1—Purification of recombinant Botulinum type A Light Chain. (A) LC1-448 was purified from *E. coli* cell paste using a Nickel affinity column as described in the methods. Protein samples (1 μl) were separated by SDS-PAGE and visualized by either staining with Coomassie blue (upper panel) or Western blotting with anti-$His_6$ antibody (lower panel). Lane 1 represents molecular weight markers. Lanes 2 and 3 represent the clarified *E. coli* extract prior to and following binding to the Nickel column. Lanes 4 and 5 represent wash fractions (20 mM Imidazole). Lanes 6-10 contain the eluted LC protein. (B) LC 1-448 and the mutant LC C430S were separated by SDS-PAGE in the absence or presence of reducing agent and visualized by staining with Coomassie blue. The arrow indicates the position of the LC1-448 dimer. (C) Cartoon showing the constructs generated in this study. (D) recLC 1-425 was purified from E. coli by a three column strategy. Protein samples were separated by SDS-PAGE and visualized by staining with Coomassie blue. The clarified extract was initially purified as for LC 1-448 using a Nickel affinity column as described in (A). The eluted material was then pooled, dialyzed against 10 mM Tris-HCl, pH 7.8, 20 mM NaCl, 10 mM imidazole and loaded onto a 150 ml column of sephacryl S-200HR. The peak fractions (fractions 33-38) were pooled and applied to a DEAE-sepharose anion exchange column. Bound proteins were eluted with a linear NaCl gradient (20-300 mM).

Botulinum neurotoxins (BoNTs) are produced by the spore-forming anaerobic bacterium *Clostridium botulinum* and are the most lethal biological poisons of man. Seven immunologically distinct BoNT serotypes (designated A-G) have been identified. Accidental exposure to BoNTs, for example through contaminated food, can result in life threatening flaccid paralysis. Further, BoNTs have been weaponized in highly toxic aerosol form, and consequently pose a significant "dual threat", both to civilian and military populations. As a result, there is an urgent need for therapeutic countermeasures against BoNTs.

BoNT is secreted as a holotoxin composed of two peptide chains that are linked by a disulfide bridge. The heavy chain is responsible for: (1) targeting and binding to surface receptors on nerve terminals; (2) translocation into the neuronal cytosol via the formation of a low pH endosome; and (3) protecting the substrate binding cleft of the light chain prior to neuronal internalization. The light chain, which dissociates from the heavy chain in the low endosomal pH, is released into the cytosol where it acts as a zinc metalloprotease that cleaves SNARE (soluble NSF-attachment protein receptor) proteins: SNAP-25 (synaptosomal-associated protein of 25 kDa), synaptobrevin, and syntaxin. BoNT serotypes A, C, and E cleave SNAP-25; serotypes B, D, F, and G cleave synaptobrevin; and serotype C can also use syntaxin as substrate. Cleavage of SNARE complexes blocks the release of acetylcholine leading to flaccid paralysis.

In one embodiment, the present invention is a method of creating a preparation of soluble and catalytically active botulinum neurotoxin type A light chain. Another embodiment of the invention is a preparation of soluble and catalytically active botulinum neurotoxin type A light chain. Another embodiment of the present invention is a method of screening inhibitors involving exposing inhibitors to the preparation described above. Another embodiment of the invention is an antibody specific for a catalytically active and soluble form of botulinum neurotoxin type A light chain.

Method of Preparing Botulinum Neurotoxin Type A Light Chain or Type E Light Chain. In one embodiment of the invention, one would prepare botulinum neurotoxin light chain type A (LC/A) by obtaining a DNA sequence encoding LC/A and deleting the C-terminal portion of the sequence so that the nucleic acid sequence encodes amino acid residues 1 through 419-447, preferably 1 through 425. For an exemplary sequence, see Dineen, et al., Curr. Microbiol. 46:345-352, 2003. Fragments comprises residues 1-424 and 1-426 are also included and are within the definition of "consisting essentially of residues 1-425."

Typically, one would use the primers described below at Table 1 of the Example to obtain the coding sequence for LC/A1-425, although primers of other lengths might be useful. One of skill in the art could easily, with reference to published nucleotide sequence for LC/A, construct primers for other embodiments of the present invention within the scope of the claims. For example, one may wish to construct LC/A1-424 or LC/A1-426.

Preferably, the PCR product of these primers would be ligated into a cloning vector, such as the TA cloning vector pGEM-T™ (Promega) and sequenced to conform the correct sequence. The insert is typically amplified and subcloned into an expression vector, such as the modified pET15b (Novagen) expression vector described in the Examples.

The Examples below describe a typical expression and purification of BoNT LC/A. For example, the Examples below describe expression of the protein in E. coli BL-21RIL (DE3) cells. An RIL strain is preferred for high expression of genes with AT sequences. RIL has tRNAs that recognize the AT codons of arginine, isoleucine and leucine (RIL).

Typically, the catalytic activity of LC/A can be demonstrated as described below in the Example. For example, the examples below show that the endopeptidase activity of the recombinent LC proteins are assayed in the mixture containing GST-SNAP 25 (described below). One may also wish to use the commercially available substrate SNAPtide™ (List Biological Laboratories), a synthetic 13 amino acid peptide that contains native cleavage site for BoNT/A. By "catalytically active" we mean that the peptide preparation of the present invention is capable of at least 90% of the catalytic activity of the peptide preparation shown in the Examples.

We show in the Examples below that LC/A1-425 has superior solubility, catalytic activity and stability. By "suitable solubility" we mean that the protein is soluble in the absence of salt or glycerol and remains soluble at 4° C. for at least two weeks with minor degradation (<10%). Table 2, below, discloses that LC/A1-425 can be obtained at least 40 mg/L culture and has suitable solubility and activity.

In another embodiment, the present invention is the product of the method described above.

In another embodiment, the present invention is preparation of LC/A that is both soluble and catalytic. In a preferred version of the present invention, the preparation comprises LC/A1-425. The preparation is both catalytically active and soluble, as defined above. In examples below, we disclose total LC/A1-425 at 40 mg/L culture after extraction and at least 33 mg/L culture after ion exchange purification.

The present invention is also a stable, soluble and catalytic preparation of LC/E wherein the C-terminal 30 amino acids are deleted. The full length LC/E is 438 amino acids. Therefore, a preferred version of the present invention consists essentially of serotype E light chain residues 1-408. By "consisting essentially of" we mean that fragments consisting of residues 1-407 and 1-409 are included.

Screen for novel small molecule inhibitors of botulinum neurotoxins. In another embodiment, the present invention is an assay used to screen LC/A or LC/E proteolytic activity using the preparations of the present invention. Preferably, this assay would use a preparation of LC/A1-425 or LC/E1-408. Preferably, the assay is a high-throughput assay.

Previous research to identify peptide and small molecule inhibitors of BoNT serotype A (BoNT/A) has targeted both holotoxin translocation and light chain (LC/A) metalloprotease activity. LC/A has been shown to be inhibited by mM concentrations of the known protease inhibitors captopril, lysinopril, and enalapril. Moreover, several small molecular weight peptides have been generated which block catalysis in the μM range. Most recently, a screen of the National Cancer Institute (NCI) Diversity set identified several compounds possessing >50% inhibition (at 20 μM concentration). Specifically, compounds structurally related to 7-chloro-4-aminoquinoline significantly inhibited LC/A at concentrations of <20 μM.

The Examples below describe an suitable throughput assay using a commercially available substrate SNAPtide™. One could of course substitute other substrates in the assay.

In a basic version of the assay, one would expose a test compound to a preparation of LC/A that is both catalytically active and soluble. In a preferred version of the assay, the LC/A preparation would comprise LC/A1-425. One would examine the catalytic activity of the LC/A preparation after exposure to the test compound. A lowering of catalytic activity would indicate that the test compound was acting as an inhibitor.

Antibody Compounds. In another embodiment, the present invention is a monoclonal or polyclonal antibody specific for the peptides of the present invention, preferably LC/A1-425. This antibody may be prepared commercially (for example, Covance, Inc.). There are multiple suitable methods for preparing mono- and polyclonal antibodies. The antibody preparation could have application as immunotherapy against botulism, as a medicinal agent to prevent diffusion of botulinum neurotoxin, as a reagent for assay of botulinum neurotoxin, and as a reagent for use in molecular biology.

EXAMPLES

Botulinum neurotoxin type A (BoNT/A) is the etiological agent responsible for botulism, a disease characterized by peripheral neuromuscular blockade. BoNT/A is produced by *Clostridium botulinum* as a single chain protein that is activated by proteolytic cleavage to form a 50 kDa Light chain (LC, 448 amino acids) and a disulfide bond linked 100 kDa Heavy chain (HC, 847 amino acids). Whilst HC comprises the receptor binding and translocation domains, LC is a $Zn^{2+}$-endopeptidase that cleaves at a single glutaminyl-arginine bond corresponding to residues 197 and 198 at the C-terminus of SNAP-25. Cleavage of SNAP-25 uncouples the neural exocytosis docking/fusion machinery.

LC/A (LC1-448) and several C-terminal deletion proteins of LC/A were engineered and expressed as His-tagged fusion proteins in *E. coli*. LC 1-448 was purified, but precipitated upon storage. Approximately 40% of LC1-448 was a covalent dimer due to the formation of inter-chain disulfide bond formation at Cys430. Conversion to Cys430 to Ser abolished dimer formation of LC1-448, but did not improve solubility. Three C-terminal deletion peptides were engineered; LC1-425 and LC1-418 were expressed and could be purified as soluble and stable proteins, whilst LC1-398 was soluble, but not stable to storage. Kinetic studies showed that LC 1-448 and LC-1-425 efficiently cleaved GST-SNAP25 and the fluorescent substrate SNAPtide™, while LC 1-418 catalyzed the cleavage of both the SNAP25 and the fluorescent substrate SNAPtide™ with a similar $K_m$, but at a 10-fold slower $k_{cat}$. Thus, regions within the C terminus of LC/A contribute to solubility, stability, and catalysis.

Subcloning Experiments

LC derivatives. Total genomic DNA from *C. botulinum* was used as a template to amplify full length LC/A (1-448), using the following primers: 5'-AGAGAGCTCATGC-CATTTGTTAATAAACAA-3' (SEQ. ID. NO: 1) and 5'-AGAGGATCCTAATGCCTTATTGTATCCTTT-3' (SEQ. ID. NO: 2). The PCR product was ligated into the TA cloning vector, pGEM-T (Promega), and sequenced to confirm the correct sequence. pGEM-LC/A was subsequently used as a template to generate expression constructs. DNA encoding LC1-448, LC1-425, LC1-418 and LC1-398 were amplified, using the indicated primers (Table 1) and subcloned into a modified pET15b (Novagen) expression vector that contained NdeI, SacI, and BamHI sites within the multicloning site for the generation of His-fusion proteins. DNA encoding pLC1-448(C430S) was generated by site directed mutagenesis of pLC1-448 using the QUIKCHANGE KIT (Stratagene) as described by the manufacturer.

Amplifications were performed in 100 μl reactions containing 20 mM Tris-HCl (pH 8.4), 50 mM KCl, 5 mM $MgCl_2$, 200 μM dNTPs, 50 ng template DNA, 100 pmoles of each primer, and 1 unit of Platinum Taq polymerase (Invitrogen). Reactions were heated to 95° C. for 10 minutes to activate the polymerase and then cycled 30 times with 1 minute denaturation at 95° C., 1 minute annealing at 58° C., and 2 minutes extension at 72° C. (10 minutes in last cycle). Products were purified using the Geneclean Spin Kit to remove excess primers, digested with the appropriate restriction endonucleases, and purified by agarose gel electrophoresis prior to ligation into the expression vector.

SNAP-25HA. pGEX-SNAP25bHA was constructed by PCR amplification of a cDNA (human SNAP25b) using the following primers: 5'-CCCGAGCTCATGGC CGAGGAC GCA GAC-3' (SEQ. ID. NO: 3) and 5'-GGG GGA TCC CTA CAA GCT GGC GTA GTC GGG CTC GCT GTA GGG GTA ACC ACT TCC CAG CAT CTT TGT TGC-3' (SEQ. ID. NO: 4) and the SacI-BamHI sites of pGEX-2T. This construction introduced the 11 amino acid HA epitope at the C terminus of SNAP-25.

Figure 1B:
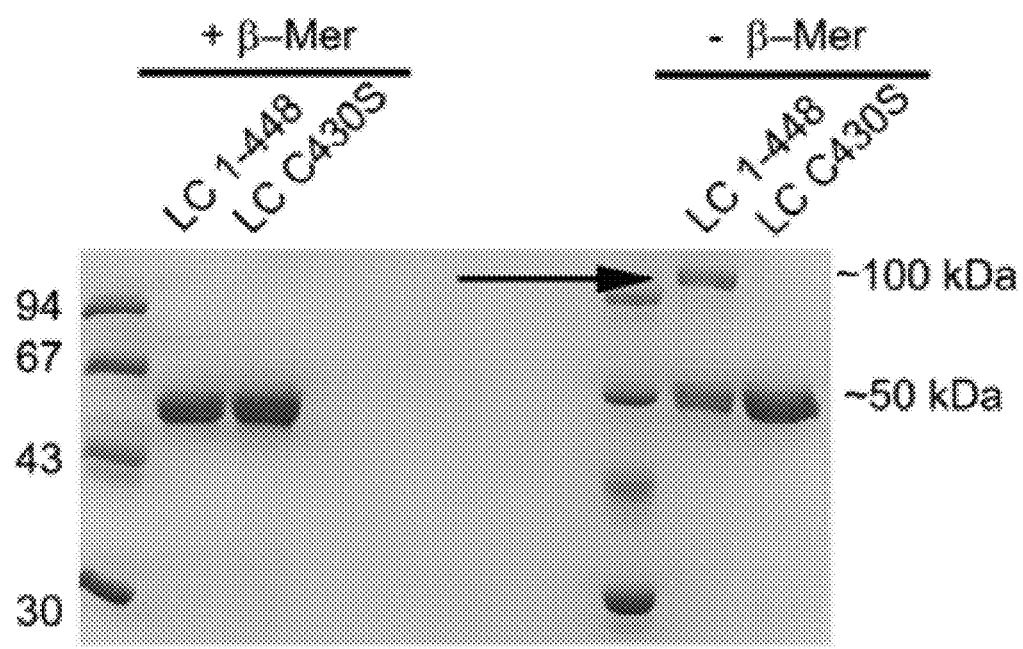

Expression and Purification of BoNT LC/A. Vectors encoding LC/A, or various LC/A derivates, were transformed into E. coli BL-21 RIL (DE3) cells (Stratagene) due to superior expression of LC/A as compared to expression in *E. coli* BL-21. *E. coli* BL-21 RIL (DE3) containing LC/A expression plasmids were grown overnight on L-agar with 100 μg/ml ampicillin and 50 μg/ml chloramphenicol. Cells were inoculated into fresh LB medium containing antibiotics, grown at 30° C. for 2.5 hours at 250 rpm to $OD_{600}$ ~0.6, induced by addition of 1 mM IPTG, and then cultured at 250 rpm overnight at 16° C. Cells were grown in 2 liter of Luria Broth (5×0.4 L cultures), and harvested cells lysed by French Press in 40 ml ice cold buffer A (10 mM imidazole, 500 mM NaCl, 20 mM Tris-HCl, pH 7.9) containing EDTA-free protease inhibitor cocktail (Sigma) and 2.5 μg/ml DNAse I and 2.5 μg/ml RNAse I. The lysate was clarified by centrifugation at 20,000×g for 30 minutes at 4° C. and subsequently passed through a 0.45 μm filter. The filtered lysate was loaded onto a column of Ni-NTA resin (5 ml bed volume) that had been equilibrated with 25 ml buffer A. The column was washed with 25 ml buffer A followed by 15 ml buffer B (20 mM imidazole, 500 mM NaCl, 20 mM Tris-HCl, pH 7.9) and then eluted with 10×1 ml buffer C (250 mM imidazole, 500 mM NaCl, 20 mM Tris-HCl, pH 7.9). Fractions were analyzed by 13.5% SDS-PAGE (FIG. 1A). Peak fractions were pooled, diluted into glycerol (50% v/v), and stored at −20° C.

LC1-425 and LC1-418 were further purified as follows. Peak fractions from the Nickel column were pooled and dialyzed for 12 hours against 10/20/10 buffer (10 mM Tris-HCl, pH 7.8, 20 mM NaCl, 10 mM Imidazole) and clarified by centrifugation at 12,000×g for 20 minutes at 4° C. The soluble dialyzed fraction contained >95% of the total LC and was subjected to gel-filtration on a Sephacryl S200 HR, 150 ml column equilibrated in 10/20/10 buffer and 2 ml vol were collected. Peak fractions as determined by SDS-PAGE were subjected to anion exchange chromatography (DEAE-sephacel, 10 ml) and bound proteins eluted with a linear gradient of 20-300 mM NaCl. Peak fractions containing LC were pooled and dialyzed overnight into 20 mM $K^+$-HEPES, pH 7.4. Purified proteins were then either stored at −20° C. in the presence of 50% glycerol v/v at ~7.5 mg LC/A/ml or undiluted at −80° C.

Cleavage of SNAP25bHA. Endopeptidase activity of the recombinant LC proteins was assayed in 40-μl reaction mixture containing: indicated concentrations of GST-SNAP25bHA and 20 nM LC/A. After incubation in reaction buffer A (20 mM $K^+$-HEPES, pH 7.4, 150 mM potassium glutamate) at 37° C., samples were withdrawn at various times and reactions were stopped by adding SDS-PAGE sample buffer. The products were resolved by electrophoresis on a 10% SDS-PAGE gel and stained with Coomassie Blue. The cleavage of SNAP-25HA was determined by densitometric scanning of the bands. Kinetic constants were derived using the EnzFitter program.

Cleavage of SNAPtide™ SNAPtide™ (FITC/DANCYL) is a synthetic 13-amino acid peptide that contains native cleavage site for BoNT/A (List Biological Laboratories). SNAPtide™ is a quenched fluorescent substrate peptide that is based on fluorescence resonance energy transfer (FRET). Initially the N-terminal fluorophore, FITC, is quenched by the C-terminal chromophore, DANCYL. Cleavage of SNAPtide™ releases the fluorophore and fluorescent enhancement was measured. Assays were carried out in a 50-μl reaction mixture containing various concentrations of SNAPtide™ and 100 nM LC/A. After incubation at 37° C. for indicated times, reactions were terminated by transfer to ice and addition of a 100 μl EDTA solution (10 mM Tris, 100 mM EDTA, pH 8.0). Samples were left to equilibrate for 30 minutes on ice prior to measurement of fluorescence at 523 nm. Control wells containing only SNAPtide™ were used to determine background fluorescence.

Circular Dichroism Analysis. The recombinant LC proteins (0.5 mg/ml) were diluted into phosphate buffered saline, pH 7.4. The choice of PBS as buffer was necessary due to stability issues in the presence of low salt conditions. The CD spectrum was recorded between 190 and 250 nm at 22° C. in a 1-mm path cuvette using a Jasco J710 spectropolarimeter. The scanning speed was set at 10 nm/min and the response time was 4 seconds. Buffer contribution was corrected.

Results

While expression of LC/A in *E. coli* has been demonstrated (Y. Li, et al., supra, 1994; H. F. LaPenotiere, et al., supra, 1995; L. Zhou, et al., supra, 1995; S. Kadkhodayan, et al. supra, 2000; L. Li and B. R. Singh, supra, 1999), poor solubility has limited the use of these constructs for biochemical and structural analysis. The ability to engineer soluble derivates of the S1 subunit of Pertussis toxin that were amenable to biochemical and biological analysis prompted a characterization of the C terminus of LC/A to determine if specific regions were responsible for the observed poor solubility of LC/A. C-terminal deletions were engineered based upon the structure and biochemical properties of BoNT and then characterized for solubility, catalysis, and stability.

Limited solubility of recombinant, full length LC/A (LC1-448). *E. coli* BL-21(DE3)(pET LC/A) had a slow growth rate at 37° C. relative to control cells and produced minimal amounts of LC/A (<0.5 mg/L of culture) after a 5 hours induction with 1 mM IPTG (Data not shown). The reason for the observed slow growth may be due to the AT rich codon usage within the LC/A open reading frame. The slow growth of *E. coli* containing LC expression plasmids has been reported (L. Li and B. R. Singh, supra, 1999).

Conditions were developed to allow high level expression of the fusion protein. Expression was optimal in a strain of *E. coli* supplemented with the rare *E. coli* arginine, isoleucine and leucine codons (BL-21 RIL). Induction at 16° C. for 18 hours allowed stable accumulation of LC 1-448 to a concentration of 25-30 mg/l culture. Furthermore, induction at 16° C. resulted in greater protein stability relative to 30° C. or 37° C. A typical purification from 2-1 culture yielded ~60 mg LC 1-448 which was >90% pure as determined by SDS-PAGE/densitometry (FIG. 1A). Western blot analysis identified many of the lower molecular weight bands as C-terminal degradation products (FIG. 1A, lower panel). Degradation could be largely inhibited by addition of metal chelators such as EDTA, suggesting breakdown was due to a metalloprotease activity. At this time, however, we cannot differentiate between an endogenous protease and autocatalytic processing of the light chain as reported by Ahmed (Ahmed et al., *J. Protein Chem.* 19:475-487, 2000).

LC 1-448 was unstable in solution forming a precipitate within 24 hours at 4° C. or immediately upon freeze-thaw. Dialysis into a range of low-high salt buffers did not improve solubility. Precipitation of the light chain has been reported previously and is hypothesized to result from protein misfolding (Kadkhodayan et al., supra, 2000). Stabilization of the protein was achieved by addition of glycerol to 50% v/v or by storage at low concentrations (<0.5 mg/ml). Previous studies in which the light chains of BoNT/B and BoNT/E were expressed in *E. coli* reported the formation of disulfides (Hanson et al., *Nat. Struct. Biol.* 7:687-692, 2000; Mira et al., *Biochemistry* 40:2234-2242, 2000). We therefore tested whether protein precipitation was due to the presence of disulfide linked light chain. Approximately 40% of the protein purifies as a disulfide linked dimer (FIG. 1B). Mutation of cysteine 430 to serine (LC C430S) abolished dimer formation, but did not improve protein solubility.

Figure 1C:
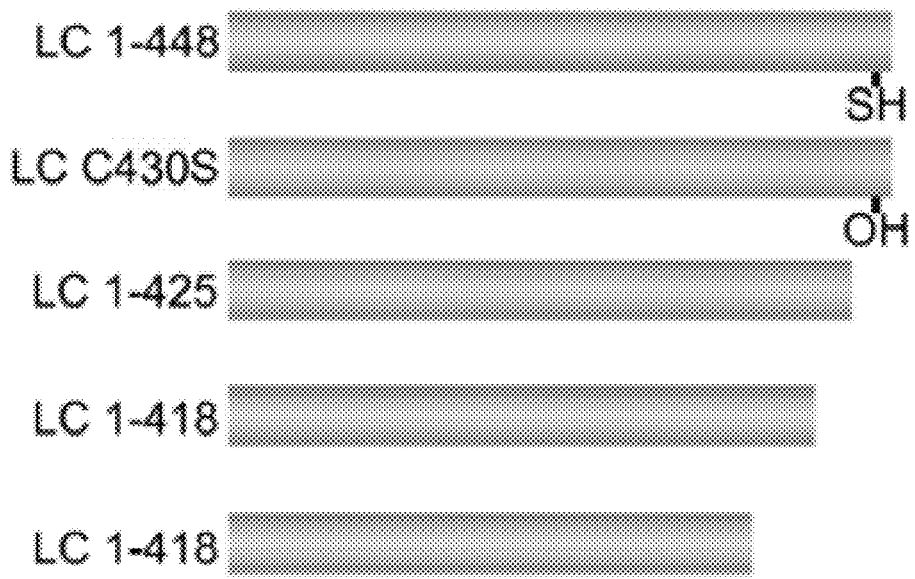

Sequential deletion of the C terminus of LC/A affects solubility and stability. Analysis of the primary amino acid sequence of LC indicated the C-terminal region was rich in both hydrophobic and charged residues and included a β-strand between residues 425 and 432. A series of C-terminal deletions of LC/A were engineered to define regions that contribute to solubility, stability, and catalysis (FIG. 1C). The initial deletion peptide was engineered to terminate LC/A after F425, yielding LC 1-425, which removed a hydrophobic β-sheet from the C terminus. Two longer deletions were engineered to terminate LC/A after N418 (LC 1-418), which corresponded to a similar deletion peptide that has been engineered within the light chain of Tetanus toxin (O. Rossetto, et al., *Toxicon.* 39:1151-1159, 2000) and after A398 (LC 1-398), which eliminated a loop region that included residues that hydrogen bonded to residues within the N terminus of LC/A.

Figure 1D:
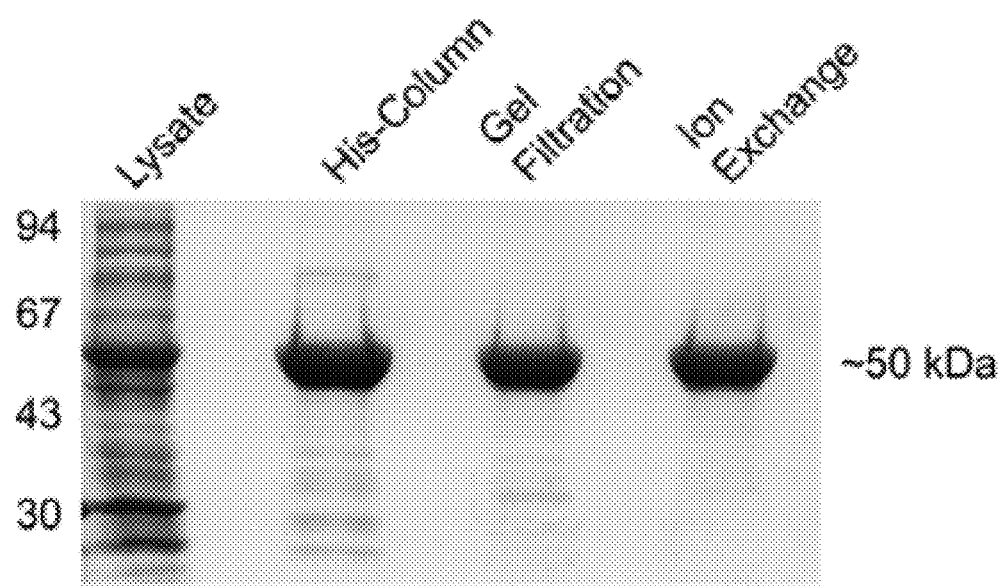

LC 1-425 was expressed at higher levels than fall length LC/A or the other C-terminal deletion peptides (~40 mg/l) and upon purification by gel filtration and ion exchange chromatography could be concentrated to >40 mg/ml (FIG. 1D). The protein was soluble in the absence of salt or glycerol and remained soluble at 4° C. for several weeks with minor degradation. LC 1-418 was expressed at levels similar to the full length protein (LC 1-448) and was also soluble when concentrated to >40 mg/ml. Relative to the other C-terminal deletion peptides, LC 1-398 was expressed at low levels and was extensively degraded upon purification (Data not shown). The expression levels, solubility and stability of the various constructs are summarized in Table 2. Based on these findings, insolubility of the LC is attributable to the C-terminal β-sheet that is involved in association with the HC within the holotoxin.

Figure 2A:
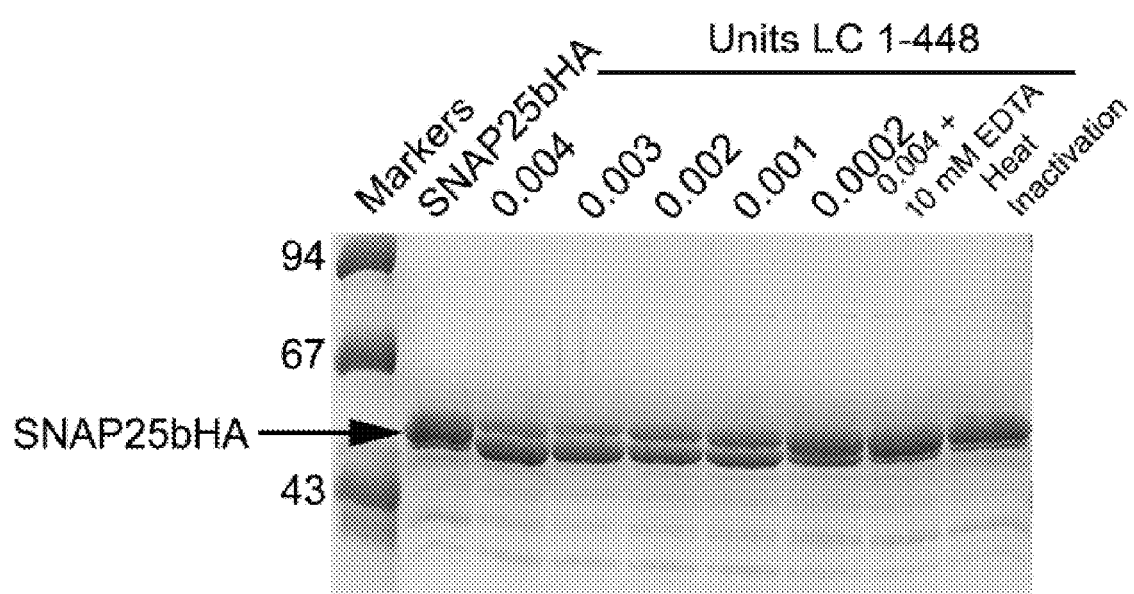
FIG. 2—Cleavage of GST-SNAP25bHA by LC 1-448. (A) GST-SNAP25HA (5 µM) was incubated for 10 minutes at 37° C. in the presence of various concentrations of LC 1-448 (250 nM-1 nM). The reactions were terminated by addition of chilled 3×SDS-PAGE buffer. Where indicated, LC 1-448 was pretreated with 10 mM EDTA for 30 minutes or heated at 75° C. for 20 minutes prior to use. The cleaved product was analyzed by SDS-PAGE and visualized by staining with Coomassie blue. (B) Graph showing initial velocity of GST-SNAP25HA cleavage by LC 1-448 as a function of substrate concentration. Inset Lineweaver-Burke plot. Kinetic studies were carried out as described utilizing substrate concentrations of 1-25 µM GST-SNAP25HA. Each concentration was run in duplicate and the experiment repeated three times. Data was analyzed using EnzFitter software to determine values for apparent $K_m$ and $K_{cat}$.
Figure 2B:
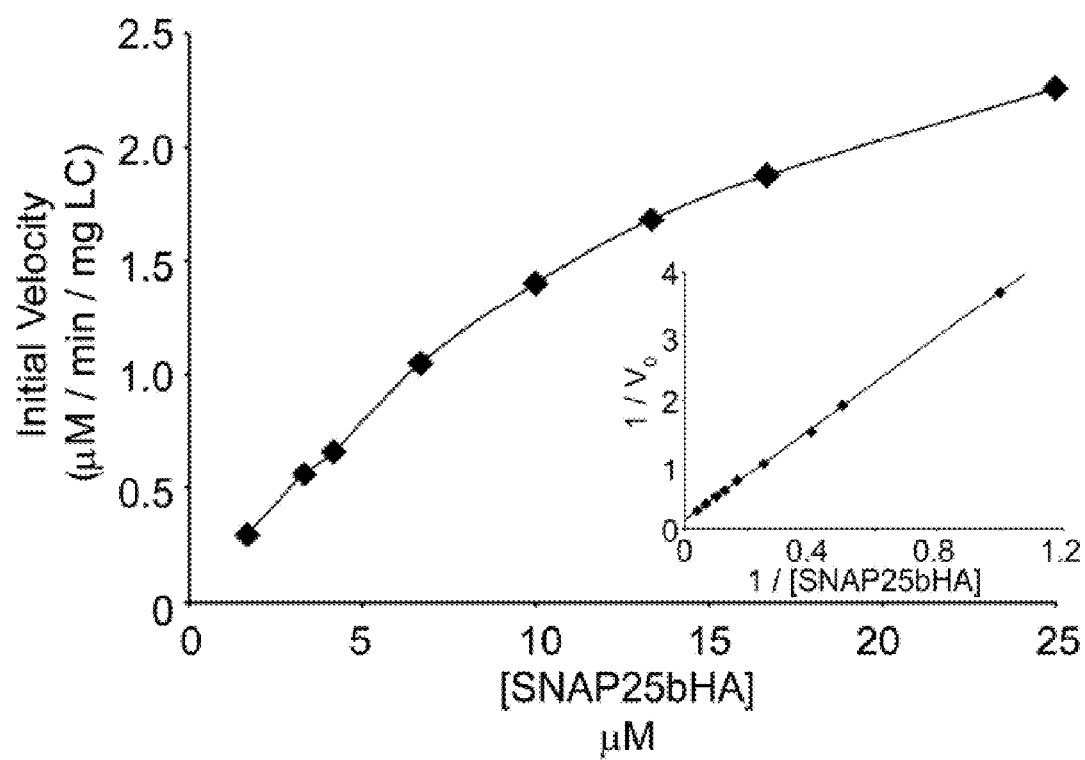

Snap25-HA is a substrate target for LC/A. It is difficult to detect the cleavage of the C-terminal 9 amino acid residues of SNAP-25 by LC/A as a shift in apparent molecular mass by SDS-PAGE and typically the cleavage product is determined indirectly by Western blot analysis to measure the loss of immunoreactivity by an antibody that recognizes the C-terminus of SNAP25 or directly by HLPC detection of the cleaved peptide (Sukonpan et al., *J. Pept. Res.* 63:181-193, 2004). Singh and coworkers described a C-terminal His-$_6$-SNAP25 that was reported to allow detection of a cleavage product (Li et al., supra, 1999). To facilitate detection of the cleavage of GST-SNAP25 by LC/A, an HA epitope was engineered at the C terminus of GST-SNAP25 which effectively changed the cleavage product of LC/A to remove a peptide of 20 amino acids. The use of GST-SNAP25 as a substrate for BoNTs does not interfere with the catalytic activity of the toxin (Hanson et al., supra, 2000). The cleavage of GST-SNAP25 by LC/A was readily detected by SDS-PAGE of the reaction mixture (FIGS. 2A and B). Western blotting demonstrated that cleavage by LC/A removed the C-terminal HA-tag, but not the N-terminal GST-tag. The calculated $K_m$ and $K_{cat}$ for GST-SNAP25 were comparable to previous reports that determined the kinetic parameters of LC/A on SNAP25 (Zhou et al., supra, 1995; Kadkhodayan et al., supra, 2000; Binz et al., *Biochemistry* 41:1717-1723, 2002, Li et al., *Biochemistry* 39:2399-2405, 2000). GST-SNAP25 was used as a target to characterize the enzymatic activity of LC/A and the C-terminal deletion peptides.

Catalytic activity of LC/A and C-terminal deletion veptides. Kinetic studies were subsequently performed using the mutant LCs, and for comparative purposes BoNT/A holotoxin. Cleavage of GST-SNAP25 by BoNT/A holotoxin was complicated by the requirement for activation prior to assay which may in part explain the variability in data generated with the holotoxin (Table 3). The presence of DTT in the assay did not affect the cleavage of SNAP25-HA by LC 1-448. The catalytic efficiency of LC 1-448 was found to be ten-fold greater than the holotoxin, which was due to a lower $K_m$ and higher reaction velocity. A previous report estimated the catalytic efficiency as within two-fold of the value for LC 1-448 (Cai et al., *Biochemistry* 40:4693-4702, 2001). Thus, the recombinant LC appears to have similar kinetic properties for SNAP25 cleavage as the holotoxin.

Figure 3:
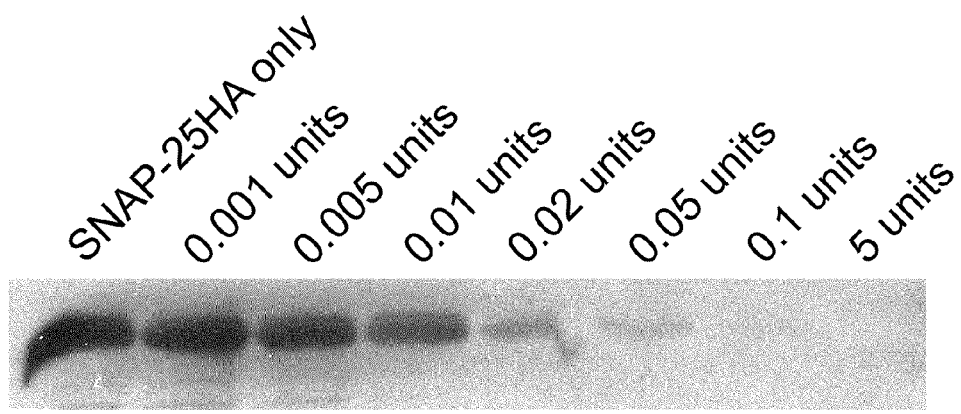
FIG. 3—Cleavage of GST-SNAP25bHA by LC 1-398. GST-SNAP25HA (2 µM) was incubated for 30 minutes at 37° C. in the presence of various concentrations of LC 1-398 (upper panel) or LC 1-448 (lower panel). Reactions were terminated by addition of chilled 3×SDS-PAGE buffer. Samples were separated on SDS-PAGE gels and visualized by Western blotting to the C-terminal HA-tag.
Figure 3:
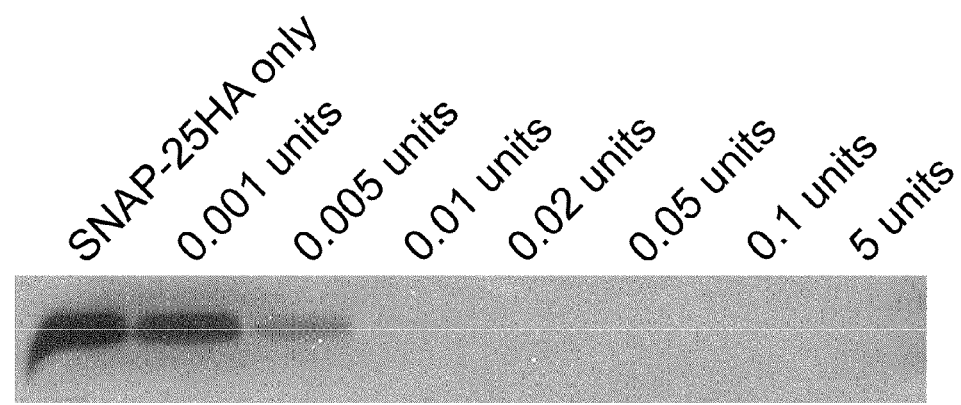

In a linear velocity reaction, the catalytic efficiency of LC 1-425 was similar to the full length LC1-448, while LC 1-418 was reduced approximately 10-fold (Table 3). The reduced rate of cleavage of SNAP25 was not due to lower substrate binding, since the $K_m$ for substrate by LC 1-448 and LC 1-418 were within 2-fold. To test whether deletion of C-terminal residues primarily affects substrate recognition or catalysis a small 13-mer peptide substrate was tested (SNAPtide™). As observed for SNAP25, the $K_m$ for the peptide was similar among the LC derivatives, but the rate of cleavage of the peptide was approximately 10-fold slower with LC 1-418 than LC 1-448 (Table 3). This implicated a role for the C-terminus in the catalytic activity of the toxin. LC 1-398 was poorly expressed and subject to extensive degradation. This made the determination of SNAP25 cleavage by SDS-PAGE impractical. However, by Western blotting against the HA-tag the rate of SNAP25 cleavage was estimated to be ~10-fold slower than LC 1-448 (FIG. 3). The reduced catalytic rate of LC 1-398 was also observed, using the SNAPtide™ peptide as substrate. Due to poor protein stability, the kinetic parameters for LC1-398 were not determined.

Figure 4:
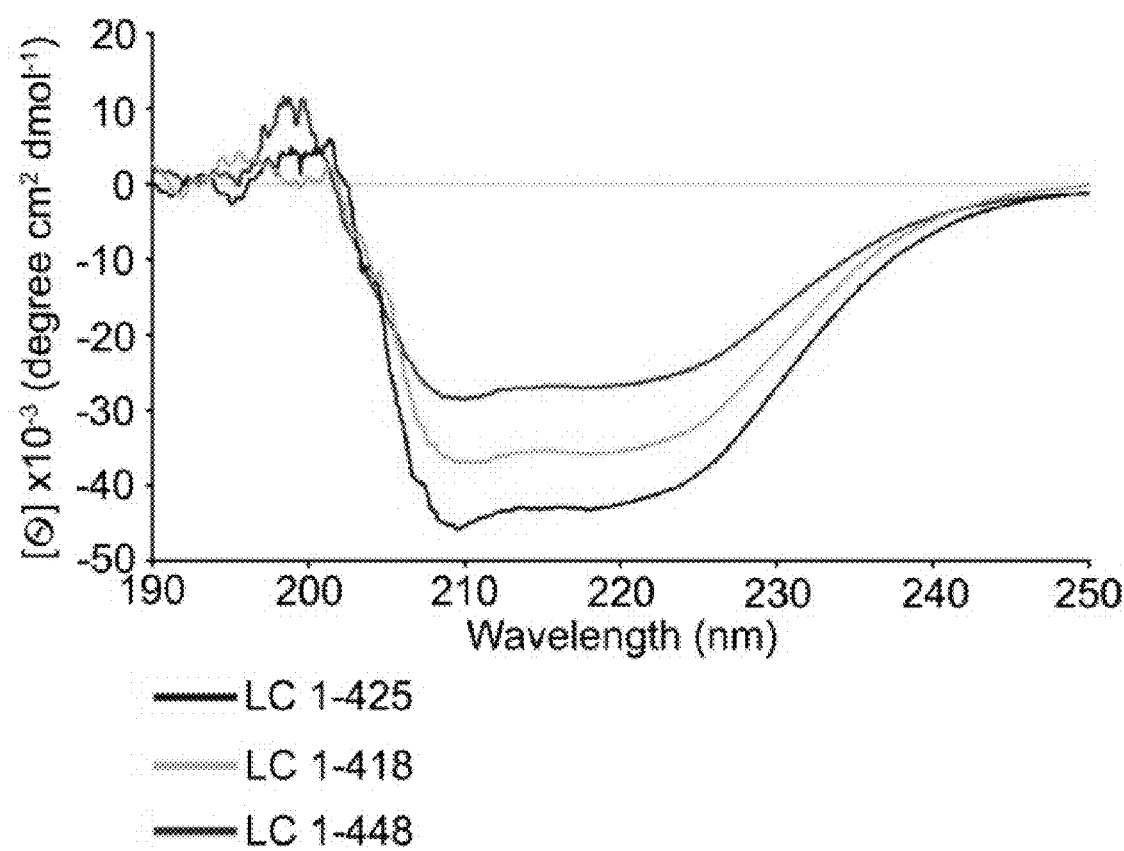
FIG. 4—Circular dichoism spectrum of recombinant LCs. The CD spectra were recorded as described under Experimental Procedures. [Θ] is the mean residue weight ellipticity. Upper curve represents LC 1-448, middle curve represents LC-1-418, and lower curve represents LC 1-425.
Figure 6:
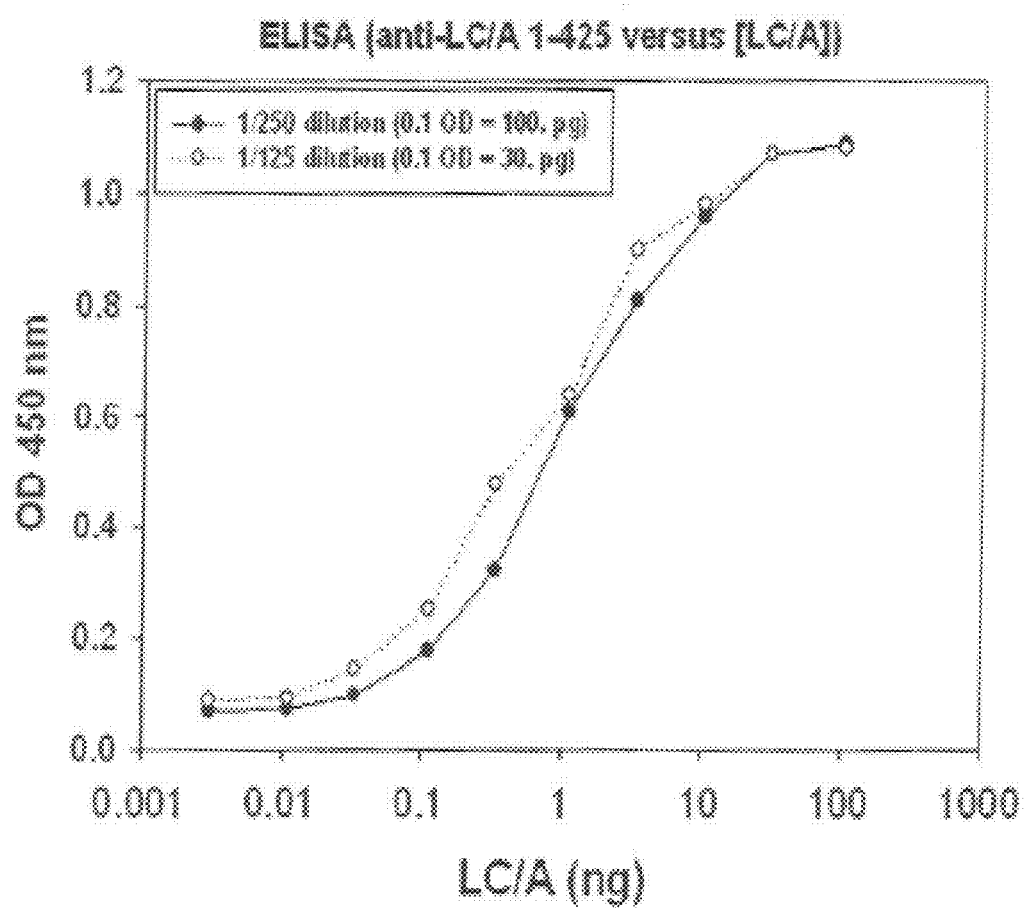
FIG. 6 is a graph of an ELISA using antibodies to the light chain of LC/A(1-425). This is a standard assay and can be modified to be more sensitive. As conducted the assay is within a few folds of the sensitivity of the mouse assay for BoNT. The polyclonal antibodies used in this titration experiment were produced by Covance, Inc., using complete Freund's adjuvant as the primary adjuvant and incomplete adjuvant in the booster immunizations.

CD spectra of LC/A and C-terminal deletion peptides. The secondary structure of globular proteins is probed by far-UV CD spectral analysis. The secondary structure of the LC derivatives was determined in 150 mM NaCl to stabilize the proteins in solution during the assay. The far-UV CD spectra corresponding to the recombinant LCs are dominated by strong minima at 209 nm and 220 nm, indicating their highly helical nature (FIG. 4).

Discussion

Botulinum neurotoxin type A (BoNT/A) is the most toxic protein known, with mouse $LD_{50}$ values of <1 pg/g. As such, study of BoNT/A has been limited by the ability to safely produce and handle large quantities of the protein. One approach in working with protein toxins is to develop variants which harness a biological/biochemical property, whilst eliminating that overall toxicity of the molecule. Isolation of non-toxic Light chain (LC/A) can be achieved through one of two approaches. The first involves the efficient separation of LC/A from the Heavy chain (HC) through chromatographic separation, a procedure which exposes the worker to significant health risk. The second approach is to express a recombinant form of the protein which can be purified to homogeneity, but was insoluble at elevated concentrations, which complicate biophysical characterizations and compromises catalytic and spectroscopic analysis.

Expression of recombinant forms of LC/A has been reported, with variable success. Microinjection of *Aplysia californica* cholinergic neurons with mRNA encoding LC/A or LC/A$^{Y9-L415}$ efficiently blocked neurotransmission (Kurazono et al., *J. Biol. Chem.* 267:14721-14729, 1992). While protein generated by in vitro translation were susceptible to degradation and internal initiation of translation, expression of LC/A in *E. coli* is complicated by solubility and stability. A maltose binding protein-LC/A fusion protein was produced in *E. coli* at 5-10 mg/l, but cleavage of the fusion protein yielded 0.5 mg/l of purified LC/a (Zhou et al., supra, 1995). LC/A was also expressed in *E. coli* with a C-terminal His-Tag, N-terminal GST- and C-terminal His-Tag or a His-Tag on both ends of the protein (Kadkhodayan et al., supra, 2000). The first two constructs were found to be unstable in solution, forming aggregates at 4° C. within a few days. The third construct displayed greater stability and could be concentrated to 6-12 mg/ml without precipitation. However, the catalytic efficiency of the LC/A was ~10-fold lower than that of the holotoxin. Li and Singh (Li et al., supra, 1999) reported expression of LC/A at ~20 mg/l which could be purified and cleaved SNAP-25 at a rate similar to the holotoxin. This was used to measure the spectroscopic and catalytic properties of the light chain and mutated forms of the light chain. In the current study, full length LC/A was also produced at similar expression levels, but precipitated upon freeze-thaw or when concentrated above 1 mg/ml, which limited its utility for structure-function studies. Deletion mapping identified β-strand comprising residues 425-432 as responsible for the limited solubility of LC/A, while residues 398-425, which intra-chain H bond, were required for LC/A catalysis and stability. Thus, LC1-425 is the minimal catalytic form of LC/A.

In a recent report Fernández-Salas et al. (Fernández-Salas et al., *Proc. Natl. Acad. Sci. USA* 101:3208-3213, 2004) identified a di-leucine motif within the C-terminus of LC/A ($\underline{E}^{424}$FYK$\underline{LL}^{429}$) (residues 424 to 429 of SEQ ID NO:14), which contributed to efficient targeting of LC/A to the plasma membrane. The role of the di-leucine motif in catalysis was unclear, since substitution of the leucine residues to arginine had limited effects on the cleavage of SNAP25 in PC-12 cells, while recombinant forms of this protein showed a 26-fold reduction in catalytic activity. Moreover, a C-terminal deletion, equivalent to LC 1-418, showed a ~80-fold decrease in activity compared to a ~10-fold decrease in this study. It is possible that the reduced catalytic activity was a due to solubility and stability issues with the recombinant proteins.

Alignment of the C terminus of the light chains of the BoNTs showed only limited primary amino acid identity, while structures of this region from BoNT/A (Lacy et al., *Nat. Struct. Biol.* 5:898-902, 1998) and Bont/B (Swaminathan et al., *Nat. Struct. Biol.* 7:693-699, 2000) indicate the C terminus is composed of an ordered loop followed by a hydrophobic β-sheet (FIG. 5). In the holotoxin, the β-sheet is linked to the heavy chain (HC) through a conserved disulfide bond and extensive hydrogen bonding. Exposure of this region in isolated LC, in the absence of the HC, may contribute to the insolubility of full length LC in solution. Several findings support this hypothesis; purified LC forms intermolecular disulfides (this study), addition of chaperones (HC, BSA) increases the solubility of LC/A (Sukonpan et al., *J. Pept. Res.* 63:181-193, 2004), deletion of this region enhances protein solubility (this study), and a recombinant LC-HC$_N$ fusion (1-871) is stable and soluble in solution (Chaddock et al., *Protein Express. Purif.* 25:219-228, 2002). From the alignment of the C termini of the BoNTs, it appears that several subgroups are identified. Thus there is the possibility of inter chain association between the LC and HC of domains of the various BoNTs within each subgroup.

Deletion mapping of the C terminus of *clostridial* toxins has resulted in conflicting data, a minimal region (LC 1-425) was determined to be required for optimal catalysis. Deletion of C-terminal residues preceding F425 has a small effect on substrate binding as judged by $K_m$ values, but causes a large decrease in catalytic efficiency. We propose that the observed decrease in catalytic efficiency is due to loss of tertiary structure. In BoNT/A and BoNT/B each loop that precedes F425 forms extensive intramolecular hydrogen bonds. These bonds stabilize the structure of both the loop region and the catalytic core. Deletions beyond F425 may therefore reduce catalysis by disrupting the intramolecular bonds required for correct orientation of the active site.

Expression of the full length LC of tetanus toxin (TeNT), residues 1-457, in *E. coli* was also possible, but underwent proteolysis resulting in cleavage of C-terminal residues (Fairweather et al., *FEBS Letts.* 323:218-222, 1993). The recombinant protein could associate with purified HC, and displayed catalytic activity, albeit at a level of 10-15% relative to the native LC purified from *C. tetani*. Further analysis revealed that the reduced activity was a result of removal of the C terminus, implicating a role for this region in catalysis. Subsequently, Montecucco et al. (Rosetto et al., supra, 2000) reported the expression of TeNT LC in *E. coli* as a GST fusion protein was unstable, purifying as three distinct polypeptides. A deletion protein, sLC (1-427) by contrast was found to be highly stable and soluble for several weeks at 4° C. The activity of sLC was higher than native LC and recombinant LC. While the molecular basis for the observed differences was not determined, alignment of the LCs of TeNT and the BoNTs (FIG. 5) suggested that the toxins have similar structure-function properties at their C termini.

The availability of active, soluble and stable derivatives of LC/A provide opportunities to better define substrate recognition, and aid in the development of small molecular weight inhibitors. The properties of LC 1-425 make it amenable to high throughput applications which are required for efficient screening of inhibitors. Moreover, the solubility of the protein should aid in the generation of co-crystals of inhibitors and LC and allow structural analysis of the extended BoNT active site.

TABLE 1

Primers used for generation of LC and LC derivatives.

| Construct | Primer set |
|---|---|
| LC 1-448 | 5'-AGAGAGCTCATGCCATTTGTTAATAAACAA-3' (SEQ. ID. NO: 1) |
| | 5'-AGAGGATCCTTACTTATTGTATCCTTTATCTAA-3' (SEQ. ID. NO: 5) |

TABLE 1-continued

| Primers used for generation of LC and LC derivatives. | |
|---|---|
| Construct | Primer set |
| LC 1-425 | 5'-AGAGAGCTCATGCCTTTGTTAATAAACAA-3' (SEQ. ID. NO: 6) |
| | 5'-AGAGGATCCTTAAAATTCAAACAATCCAGTAAA-3' (SEQ. ID. NO: 7) |
| LC 1-418 | 5'-AGAGAGCTCATGCCATTTGTTAATAAACAA-3' (SEQ. ID. NO: 8) |
| | 5'-AGAGGATCCTTAATTTTTTAGTTTAGTAAAATT-3' (SEQ. ID. NO: 9) |
| LC 1-398 | 5'-AGAGAGCTCATGCCATTTGTTAATAAACAA-3' (SEQ. ID. NO:10) |
| | 5'-AGAGGATCCTTATGCTAAATTTGTATTTCTTAA-3' (SEQ. ID. NO: 11) |
| LC C430S | 5'-GAATTTTATAAGTTGCTAAGTGTAAGAGGGATAATAACTTCT-3' (SEQ. ID. NO: 12) |
| | 5'-AGAAGTTATTATCCCTCTTACACTTAGCAACTTATAAAATTC-3' (SEQ. ID. NO: 13) |

TABLE 2

Properties of LC/A and C-terminal LC/A deletion peptides.

| Protein | ~Yield (mg/l culture) | Stability | Solubility | Activity |
|---|---|---|---|---|
| LC 1-448 | 25 | + | +/− | ++ |
| LC C430S | 25 | + | +/− | ++ |
| LC 1-425 | 40 | + | +/+ | ++ |
| LC 1-418 | 25 | + | +/+ | + |
| LC 1-398 | 10 | − | +/+ | + |

TABLE 3

Purification of LC1-425.

| LC 1-425 | Total LC 1-425 (mg/l culture)[a] | Total protein (mg/l culture)[b] | Purification Factor[b] | Yield (%) |
|---|---|---|---|---|
| Extraction | 40 | 556 | 1 | 100 |
| Ni-NTA | 36 | 41 | 14 | 90 |
| Gel filtration | 33 | 36 | 15 | 83 |
| Ion exchange | 33 | 33 | 17 | 83 |

[a]Estimated from band intensity on SDS-PAGE
[b]Based on total protein content

TABLE 4

Kinetic parameters for LC/A and C-terminal deletion peptides of LC/A.

| | GST-SNAP25Bha | | | | SNAPtide Peptide | |
|---|---|---|---|---|---|---|
| Protein | $V_{max}$ (μM/min/mg) | $K_m$ (μM) | $K_{cat}$ ($sec^{-1}$) | $K_{cat}/K_m$ ($sec^{-1}$ $\mu M^{-1}$) | $K_m$ (μM) | Relative rate[a] |
| LC 1-448 | 4.6 +/− 0.2 | 14.2 +/− 0.3 | 3.8 | 0.27 | 54.1 +/− 1.5 | 1 |
| LC C430S | 4.3 +/− 0.2 | 12.3 +/− 0.3 | 3.6 | 0.29 | 52.6 +/− 3.6 | 0.98 |
| LC 1-425 | 7.1 +/− 0.3 | 17.1 +/− 0.4 | 5.9 | 0.35 | 41.2 +/− 3.4 | 0.89 |
| LC 1-418 | 0.7 +/− 0.3 | 26.3 +/− 0.7 | 0.6 | 0.02 | 38.1 +/− 3.9 | 0.07 |
| LC 1-398 | N.D.[b] | N.D. | N.D. | N.D. | 79.9 +/− 1.1 | N.D |
| BoNT/A | 1.2 +/− 2.1 | 64 +/− 12 | 1.0 | 0.02 | N.D. | N.D. |
| BoNT/A[c] | N.D. | 51 +/− 15 | 10.2 | 0.20 | N.D. | N.D. |

[a]Rates were determined as fluorescent units/min and reported relative to values obtained for LC 1-448
[b]Not Determined due to poor stability velocity values for LC 1-398 could not be derived
[c]Values from Cai and Singh (Cai and Singh, supra, 2001).

High-Throughput Screening

A high-throughput assay used to screen LC/A proteolytic activity utilized the commercially available substrate SNAPtide™ (List Biologicals). SNAPtide™ is a synthetic 13-amino acid peptide that contains native cleavage site for BoNT/A. SNAPtide™ is a quenched fluorescent substrate peptide that is based on fluorescence resonance energy transfer (FRET). Initially the N-terminal fluorophore, FITC, is quenched by the C-terminal chromophore, DANCYL. Cleavage of SNAPtide™ releases the fluorophore resulting in increased fluorescence.

Liquid transfers were performed with automated dispensers. Recombinant LC/A (residues 1-425) was diluted to 300 nM in 30 mM Hepes-KOH, 190 mM potassium glutamate, 0.5% w/v BSA, pH 7.4. Test compounds were dissolved in methyl sulfoxide to a final concentration of 5 mg/ml. 100 nl of each compound was transferred into the corresponding wells of a 384 well plate containing 25 μl SNAPtide™ solution in 30 mM Hepes-KOH, 190 mM potassium glutamate, 0.5% w/v BSA, pH 7.4. 5 μl recombinant LC/A (residues 1-425) was then added and mixed for final concentrations of 50 nM LC/A and 1 μM SNAPtide™. Controls (SNAPtide™ alone/SNAPtide™+LC/A), 16 wells each, were included on every plate analyzed. After incubation for 60 minutes at 37° C. fluorescence was measured in a Perkin Elmer Envision.

Data Analysis

The efficacy of each compound was determined by calculation of the activity of LC/A in the presence of compound relative to the activity of LC/A alone. Control samples—consisting of SNAPtide™ alone; were used to determine the background fluorescence in the assay and subtracted from test wells. Screening positives were defined by cut-off ranges as follows:

W (weak inhibition): Activity of LC/A in the presence of inhibitor ≦75%≧61% relative to LC/A alone.

M (medium inhibition): Activity of LC/A in the presence of inhibitor ≦60%≧246% relative to LC/A alone.

S (strong inhibition): Activity of LC/A in the presence of inhibitor ≦45% relative to LC/A alone.

Table 4 is a graph of an ELISA using antibodies to the light chain of LA/A to LC/A. This is a standard assay and can be modified to be more sensitive. As conducted, this assay is within a few-folds of the sensitive of the mouse assay for BoNT.

Six compounds were identified that yielded >80% inhibition of cleavage of the SNAPtide substrate.

REFERENCES

1. Ahmed et al., *J. Protein Chem.* 19:475-487, 2000.
2. Binz et al., *Biochemistry* 41:1717-1723, 2002.
3. Cai et al., *Biochemistry* 40:4693-4702, 2001.
4. Chaddock et al., *Protein Express. Purif.* 25:219-228, 2002.
5. Collier, *Toxicon.* 39:1793-1803, 2001.
6. Dineen et al., *Curr. Microbiol.* 46:345-352, 2003.
7. Dong et al., *J. Cell Biol.* 162:1293-1303, 2003.
8. Fairweather et al., *FEBS Letts.* 323:218-222, 1993.
9. Fernández-Salas et al., *Proc. Natl. Acad. Sci. USA* 101:3208-3213, 2004.
10. Hanson et al., *Nat. Struct. Biol.* 7:687-692, 2000.
11. Lacy et al., *J. Mol. Biol.* 291:1091-1104, 1999.
12. Lacy et al., *Nat. Struct. Biol.* 5:898-902, 1998.
13. LaPenotiere et al., *Toxicon.* 33:1383-1386, 1995.
14. Kadkhodayan et al., *Protein Express. Purif.* 19:125-130, 2000.
15. Kurazono et al. *J. Biol. Chem.* 267:14721-14729, 1992.
16. Li et al., *Biochemistry* 33:7014-7020, 1994.
17. Li et al., *Biochemistry* 39:2399-2405, 2000.
18. Li et al., *Protein Express. Purif.* 17:339-344, 1999.
19. Minton, *Curr. Top. Microbiol. Immunol.* 195:161-194, 1995.
20. Mira et al., *Biochemistry* 40:2234-2242, 2000.
21. Oguma et al., *Microbiol. Immunol.* 39:161-168, 1995.
22. Popoff et al., Structural and genomic features of clostridial neurotoxins, in: J. E. Alouf, J. H. Freer (Eds.) Comprehensive Sourcebook of Bacterial Protein Toxins, Academic, London, 1999.
23. Rossetto et al., *Toxicon.* 39:1151-1159, 2000.
24. Sakaguchi, *Pharmacol. Ther.* 19:165-194, 1983.
25. Schiavo et al., *Physiol. Rev.* 80:717-766, 2000.
26. Sukonpan et al., *J. Pept. Res.* 63:181-193, 2004.
27. Swaminathan et al., *Nat. Struct. Biol.* 7:693-699, 2000.
28. Zhou et al., *Biochemistry* 34:15175-15181, 1995.

We claim:

1. A preparation of a catalytically active botulinum toxin light chain consisting of amino acid residues selected from the group consisting of 1-407, 1-408 and 1-409 of botulinum toxin light chain E from *Clostridium botulinum* strains.

2. The preparation of claim 1 wherein the preparation consists of amino acid residues 1-408 of botulinum toxin light chain E from *Clostridium botulinum* strains.

3. A method of providing a catalytically active, soluble preparation of botulinum toxin light chain E, from *Clostridium botulinum* strains comprising:
   (a) obtaining an expression vector comprising a DNA sequence encoding an amino acid sequence consisting of residues selected from the group of 1 through 407, 1 through 408 and 1 through 409 of light chain type E from *Clostridium botulinum* strains, and
   (b) expressing a polypeptide.

* * * * *

UNITED STATES PATENT AND TRADEMARK OFFICE
CERTIFICATE OF CORRECTION

| | | |
|---|---|---|
| PATENT NO. | : 7,833,524 B2 | Page 1 of 1 |
| APPLICATION NO. | : 12/273157 | |
| DATED | : November 16, 2010 | |
| INVENTOR(S) | : Eric A. Johnson et al. | |

It is certified that error appears in the above-identified patent and that said Letters Patent is hereby corrected as shown below:

Column 4, line 56 "conform" should be -- confirm --

Column 9, line 30 "fall" should be -- full --

Column 10, lines 7-8 "veptides" should be -- peptides --

Signed and Sealed this
Twenty-second Day of February, 2011

David J. Kappos
*Director of the United States Patent and Trademark Office*

SEQUENCE LISTING

<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1
agagagctca tgccatttgt taataaacaa                                    30

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide -continued

```
<400> SEQUENCE: 2
agaggatcct aatgccttat tgtatccttt                                   30

<210> SEQ ID NO 3
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 3
cccgagctca tggccgagga cgcagac                                      27

<210> SEQ ID NO 4
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 4 ggggatccc tacaagctgg cgtagtcggg ctcgctgtag gggtaaccac ttcccagcat   60
ctttgttgc                                                          69

<210> SEQ ID NO 5
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 5
agaggatcct tacttattgt atcctttatc taa                               33

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6
agagagctca tgccatttgt taataaacaa                                   30

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 7
agaggatcct taaaattcaa acaatccagt aaa                               33

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 8
agagagctca tgccatttgt taataaacaa                                   30
```

-continued

```
<210> SEQ ID NO 9
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 9
agaggatcct taattttta gtttagtaaa att                              33

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 10
agagagctca tgccatttgt taataaacaa                                 30

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 11
agaggatcct tatgctaaat ttgtatttct taa                             33

<210> SEQ ID NO 12
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 12
gaattttata agttgctaag tgtaagaggg ataataactt ct                   42

<210> SEQ ID NO 13
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 13
agaagttatt atccctctta cacttagcaa cttataaaat tc                   42

<210> SEQ ID NO 14
<211> LENGTH: 1296
<212> TYPE: PRT
<213> ORGANISM: Clostridium botulinum

<400> SEQUENCE: 14

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60
```

```
Ala Lys Gln Val Pro Val Ser Tyr Tyr Asp Ser Thr Tyr Leu Ser Thr
 65              70                  75                  80

Asp Asn Glu Lys Asp Asn Tyr Leu Lys Gly Val Thr Lys Leu Phe Glu
             85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480
```

-continued

```
Ile Thr Ser Asp Thr Asn Ile Glu Ala Ala Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
            770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895
```

-continued

```
Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275
```

```
Gly Cys Ser Trp Glu Phe Ile Pro Val Asp Asp Gly Trp Gly Glu
    1280                1285                1290
Arg Pro Leu
    1295
```

<210> SEQ ID NO 15
<211> LENGTH: 25
<212> TYPE: PRT
<213> ORGANISM: Clostridium botulinum

<400> SEQUENCE: 15

```
Thr Lys Leu Lys Asn Phe Thr Gly Leu Phe Glu Phe Tyr Lys Leu Leu
1               5                   10                  15
Cys Val Arg Gly Ile Ile Thr Ser Lys
            20                  25
```

<210> SEQ ID NO 16
<211> LENGTH: 23
<212> TYPE: PRT
<213> ORGANISM: Clostridium botulinum

<400> SEQUENCE: 16

```
Glu Glu Ile Ser Lys Glu His Leu Ala Val Tyr Lys Ile Gln Met Cys
1               5                   10                  15
Lys Ser Val Lys Ala Pro Gly
            20
```

<210> SEQ ID NO 17
<211> LENGTH: 25
<212> TYPE: PRT
<213> ORGANISM: Clostridium botulinum

<400> SEQUENCE: 17

```
Glu Glu Ile Ser Leu Glu His Leu Val Ile Tyr Arg Ile Ala Met Cys
1               5                   10                  15
Lys Pro Val Met Tyr Lys Asn Thr Gly
            20                  25
```

<210> SEQ ID NO 18
<211> LENGTH: 24
<212> TYPE: PRT
<213> ORGANISM: Clostridium botulinum

<400> SEQUENCE: 18

```
Lys Val Asn Pro Glu Asn Met Leu Tyr Leu Phe Thr Lys Phe Cys His
1               5                   10                  15
Lys Ala Ile Asp Gly Arg Ser Leu
            20
```

<210> SEQ ID NO 19
<211> LENGTH: 20
<212> TYPE: PRT
<213> ORGANISM: Clostridium botulinum

<400> SEQUENCE: 19

```
Lys Leu Ser Ser Glu Ser Val Val Asp Leu Phe Thr Lys Val Cys Leu
1               5                   10                  15
Arg Leu Thr Lys
            20
```

```
<210> SEQ ID NO 20
<211> LENGTH: 23
<212> TYPE: PRT
<213> ORGANISM: Clostridium botulinum

<400> SEQUENCE: 20

Thr Pro Ile Thr Gly Arg Gly Leu Val Lys Lys Ile Ile Arg Phe Cys
1               5                   10                  15

Lys Asn Ile Val Ser Val Lys
            20

<210> SEQ ID NO 21
<211> LENGTH: 24
<212> TYPE: PRT
<213> ORGANISM: Clostridium botulinum

<400> SEQUENCE: 21

Asp Ser Ile Pro Asp Lys Gly Leu Val Glu Lys Ile Val Lys Phe Cys
1               5                   10                  15

Lys Ser Val Ile Pro Arg Lys Gly
            20

<210> SEQ ID NO 22
<211> LENGTH: 25
<212> TYPE: PRT
<213> ORGANISM: Clostridium botulinum

<400> SEQUENCE: 22

Phe Arg Asn Val Asp Gly Ser Gly Leu Val Ser Lys Leu Ile Gly Leu
1               5                   10                  15

Cys Lys Lys Ile Ile Pro Pro Thr Asn
            20                  25
```